(12) United States Patent
Hasenberg et al.

(10) Patent No.: US 7,399,893 B2
(45) Date of Patent: Jul. 15, 2008

(54) PROCESS AND CATALYST FOR SYNTHESIS OF MERCAPTANS AND SULFIDES FROM ALCOHOLS

(75) Inventors: Daniel M. Hasenberg, Humble, TX (US); Mitchell D. Refvik, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 11/302,038

(22) Filed: Dec. 13, 2005

(65) Prior Publication Data

US 2007/0135658 A1  Jun. 14, 2007

(51) Int. Cl.
*C07C 921/00* (2006.01)
(52) U.S. Cl. .................................................. 568/924
(58) Field of Classification Search ............... 568/61, 568/71–72; 502/315
See application file for complete search history.

(56) References Cited

U.S. PATENT DOCUMENTS

| 3,035,097 | A |   | 5/1962  | Deger          |         |
|-----------|---|---|---------|----------------|---------|
| 3,697,602 | A |   | 10/1972 | Schreyer et al.|         |
| 3,963,785 | A |   | 6/1976  | Kubicek        |         |
| 3,994,980 | A | * | 11/1976 | Kubicek        | 568/61  |
| 4,059,504 | A | * | 11/1977 | Bauer          | 208/255 |
| 4,591,429 | A | * | 5/1986  | Ho et al.      | 208/254 H |
| 4,837,193 | A | * | 6/1989  | Akizuki et al. | 502/242 |
| 5,106,484 | A | * | 4/1992  | Nadler et al.  | 208/91  |
| 5,283,369 | A | * | 2/1994  | Clark et al.   | 568/71  |
| 5,352,838 | A |   | 10/1994 | Sattich        |         |
| 5,453,544 | A |   | 9/1995  | Giacobbe       |         |
| 5,733,836 | A |   | 3/1998  | Stinn et al.   |         |
| 5,874,630 | A | * | 2/1999  | Cook et al.    | 568/71  |
| 5,898,012 | A |   | 4/1999  | Stinn et al.   |         |
| 6,037,306 | A | * | 3/2000  | Xia et al.     | 502/315 |
| 6,198,003 | B1|   | 3/2001  | Lin et al.     |         |

FOREIGN PATENT DOCUMENTS

| EP | 0354460 A1 | 2/1990  |
| EP | 0564706 A1 | 10/1993 |
| EP | 0796656 A1 | 9/1997  |
| EP | 1005906 A1 | 6/2000  |

OTHER PUBLICATIONS

International Search Report and Written Opinion, PCT/US2006/047335, Jun. 5, 2007, 10 pages.

* cited by examiner

*Primary Examiner*—Yvonne Eyler
*Assistant Examiner*—M Louisa Lao (57) ABSTRACT

A process and catalyst blend for selectively producing mercaptans and sulfides from alcohols. The alcohol is reacted with hydrogen sulfide, in the presence of a catalyst blend containing a hydrotreating catalyst and a dehydration catalyst to convert the alcohol to mercaptan or sulfide in one-pass. The alcohols can include primary and secondary alcohols. The mercaptan or sulfide having less than about 30% unreacted alcohol contained therein.

15 Claims, 3 Drawing Sheets

PROCESS AND CATALYST FOR SYNTHESIS OF MERCAPTANS AND SULFIDES FROM ALCOHOLS

TECHNICAL FIELD OF THE INVENTION

The present invention relates to a process for selective production of mercaptans and sulfides from alcohols. More specifically, the present invention relates to a process for selectively producing mercaptans and sulfides from alcohols utilizing a blend of catalysts.

BACKGROUND OF THE INVENTION

Mercaptans, which are also known as thiols, are organic compounds that are used in diverse applications. Some mercaptans are used as pipeline gas odorants, agricultural supplements, or as polymerization process modifiers. When mercaptans are present in large quantities, they are generally considered to be malodorous and highly undesirable. But in low concentrations these same compounds are used as fragrances and flavorings. When used in this manner they can be an effective and economical replacement of more expensive natural products in a wide variety of perfumed articles such as soaps, detergents, powders, perfume and cologne, and even as flavoring agents. For example, mercaptans are commonly used in perfumes and cleaning supplies to impart a lavender scent. In foods and other products, mercaptan compounds are widely used to reproduce the taste and fragrance associated with black currant or grapefruit.

The variety of tastes and flavorings available can be attributed to the numerous mercaptan compounds that can be synthesized. Yet, while numerous compounds can be made, economical processes for the production of even relatively simple mercaptans are not available in some cases. In other cases, the purity of known processes require difficult separation steps to obtain mercaptans of a desired purity.

A common process to produce mercaptans is by catalytically reacting an olefin with hydrogen sulfide in the presence of a solid acid catalyst. One drawback to this typical type of reaction is that the raw material costs associated with olefins can be high. In order to reduce raw material costs, prior attempts have been made to produce mercaptans from cheaper raw materials, such as alcohols. Water is a product of reaction in the synthesis of mercaptans from alcohols. Generally, one mole of water is produced for each mole of mercaptan produced. Because the solid acid catalysts that are used for converting olefins to mercaptans can be poisoned by moisture, they are not suitable for use in synthesis of mercaptans from alcohols.

A need exists for a process for selective production of mercaptans from alcohols that results in essentially complete conversion of the alcohol to the desired mercaptan. A further need exists for a process that achieves essentially complete conversion of the alcohol to the mercaptan in one process step.

SUMMARY OF THE INVENTION

In view of the foregoing, the present invention provides a process for the selective production of a mercaptan or a sulfide from an alcohol. The process includes the step of contacting the alcohol, in the presence of a catalyst blend, with a sulfur compound reactant to produce the mercaptan or the sulfide. In an aspect, the process is performed under near isothermal conditions. The sulfur compound reactant generally has a formula of H—R—S with R being H (hydrogen) or an alkyl group. To produce a mercaptan, R is H. To produce a sulfide, R is the alkyl group.

In one aspect, the catalyst blend includes a hydrotreating catalyst and a dehydration catalyst. In another aspect, the catalyst blend includes a hydrotreating catalyst and an alumina diluent. The resulting mercaptan or sulfide that is produced has less than about 30 wt. % unreacted alcohol contained therein.

The present invention also includes a process for selective production of the mercaptan or the sulfide using a catalyst blend having a volumetric ratio of the hydrotreating catalyst to the dehydration catalyst or the alumina diluent that increases from a reactor vessel inlet to a reactor vessel outlet in order to maintain near isothermal conditions during reaction of the alcohol and the sulfur compound reactant. The sulfur compound reactant has a formula of H—R—S and is used to produce the mercaptan or the sulfide having less than about 30 wt. % unreacted alcohol. In some embodiments, R is H; or alternatively, R is an alkyl group.

In an aspect, the hydrotreating catalyst is an oxide of molybdenum and an oxide of cobalt supported on alumina. In another aspect, the hydrotreating catalyst is an oxide of molybdenum and an oxide of nickel supported on alumina. In an aspect, the alumina diluent is an alpha ($\alpha$)-alumina. In an aspect, the dehydration catalyst is a gamma ($\gamma$)-alumina.

BRIEF DESCRIPTION OF THE DRAWINGS

So that the features, advantages and objects of the invention can be understood in more detail, a more particular description of the invention briefly summarized above can be had by reference to the embodiments illustrated in the appended drawings, which form a part of this specification. The drawings illustrate only particular embodiments of the invention and are therefore not to be considered limiting of the invention's scope as it can admit to other equally effective embodiments.

DETAILED DESCRIPTION OF THE INVENTION

All references herein to elements or metals belonging to a certain Group refer to the Periodic Table of the Elements published and copyrighted by CRC Press, Inc., 1999. References to the Group or Groups shall be to the Group or Groups as reflected in this Periodic Table of the Elements using the IUPAC system for numbering groups.

Figure 1:
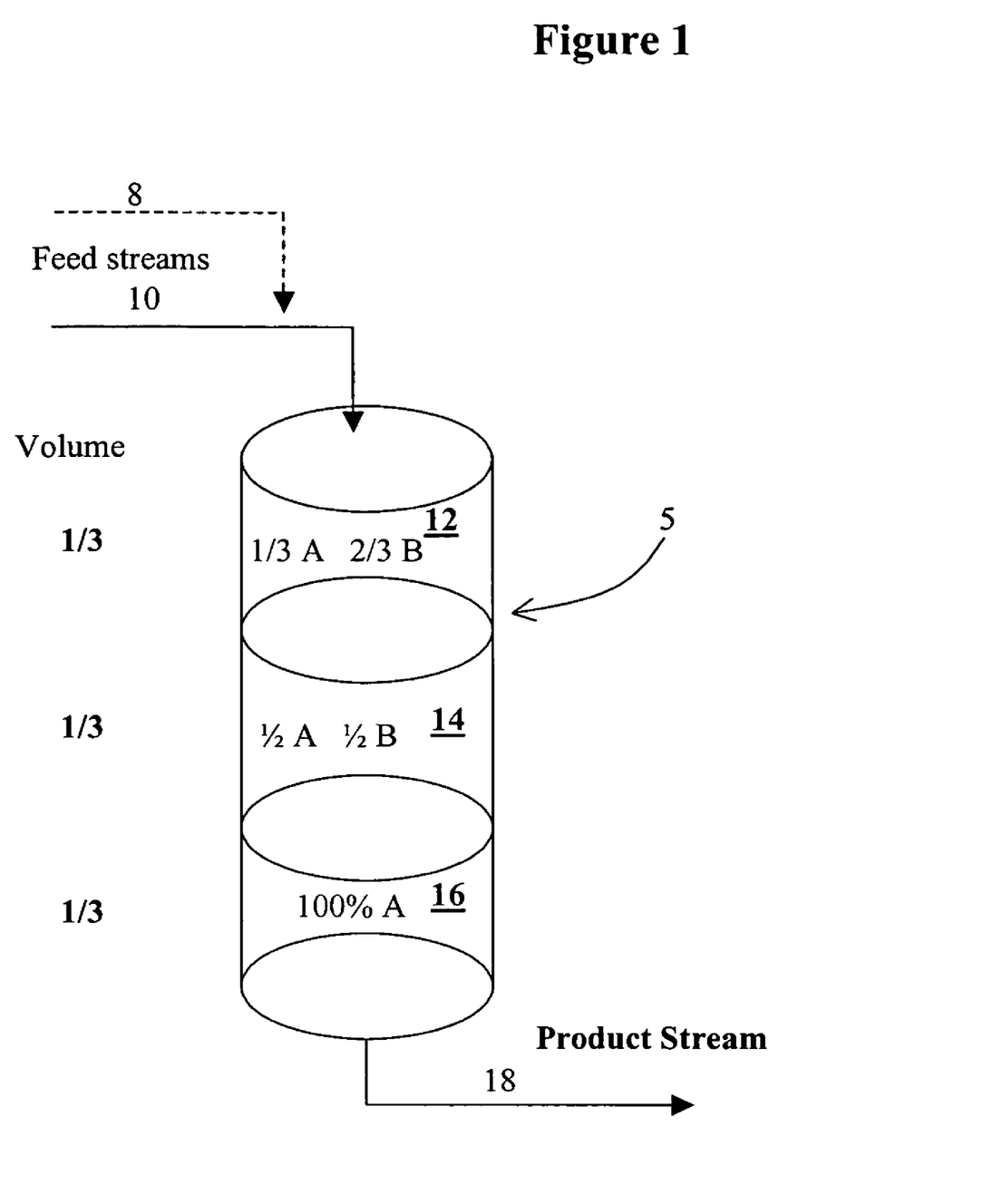
FIG. 1 is a perspective view of a catalyst bed containing a catalyst blend that is used to selectively produce a mercaptan, such as ethanethiol (ethyl mercaptan) or cyclohexanethiol (cyclohexyl mercaptan), from a corresponding alcohol in one process step in accordance with an embodiment of the present invention.

The present invention provides a process for the selective production of a mercaptan or a sulfide from an alcohol. As shown in FIG. 1, the process includes the step of contacting the alcohol feed stream 8, in the presence of a catalyst blend 5, with a sulfur compound reactant stream 10 to produce the mercaptan or the sulfide stream 18. The mercaptan or sulfide stream 18 typically contains less than about 30% unreacted alcohol. The catalyst blend 5 includes a hydrotreating catalyst A and a dehydration catalyst B. The mercaptan or sulfide stream 18 is referred to herein as a "product" stream. Use of the term "product" is not intended to imply that the mercaptan or sulfide stream 18 has been refined or finished. The mercaptan or sulfide "product" stream 18 can be sent to such finishing processes, such as fractionation, as needed.

The sulfur compound reactant generally has a formula of H—R—S. When the desired product stream 18 is the mercaptan, R is H. When the desired product stream 18 is the sulfide, R is an alkyl group.

The alcohol feed stream 8 and the sulfur compound reactant stream 10 can be fed separately or can be combined and fed together to the catalyst blend 5. To reduce the potential of catalyst poisoning or fouling, when being fed separately, the sulfur compound reactant stream 10 can be fed first to help pre-sulfide the catalyst blend 5 prior to supplying the alcohol feed stream 8. Other suitable means for pre-sulfiding the catalyst blend 5 will be apparent to those of ordinary skill in the art and are to be considered within the scope of the present invention.

In some embodiments, the alcohol feed stream 8 and the sulfur compound reactant stream 10 are reacted under near isothermal conditions. As used herein, the term "near isothermal" is defined as maintaining an operating temperature across the catalyst blend 5 within a 5° C. differential across the catalyst blend 5. In other words, the operating temperature of the catalyst blend 5 is maintained within ±/−5° C. of an inlet operating temperature of the catalyst blend 5. The reaction of the alcohol feed stream 8 with the sulfur compound reactant stream 10 in the presence of the hydrotreating catalyst A is an exothermic reaction. The reaction of the alcohol feed stream 8 with the sulfur compound reactant stream 10 in the presence of the dehydration catalyst B is an endothermic reaction. By using both the hydrotreating catalyst A and the dehydration catalyst B, the net enthalpy change for the combined reactions is relatively low, which enables the mercaptan or sulfide synthesis reaction to proceed under near isothermal conditions. The enthalpy change for the exothermic and the endothermic reactions essentially cancel each other out to provide for near isothermal conditions.

In embodiments of the present invention, as shown in FIG. 1, the catalyst blend 5 includes about 40% by volume to about 95% by volume hydrotreating catalyst A and about 5% by volume to about 60% by volume dehydrating catalyst B. In some embodiments, the catalyst blend 5 includes about 40% by volume to about 80% by volume hydrotreating catalyst A and about 20% by volume to about 60% by volume dehydrating catalyst B. In other embodiments, the catalyst blend 5 includes about 45% by volume to about 75% by volume hydrotreating catalyst A and about 25% by volume to about 55% by volume dehydrating catalyst B.

Figure 2:
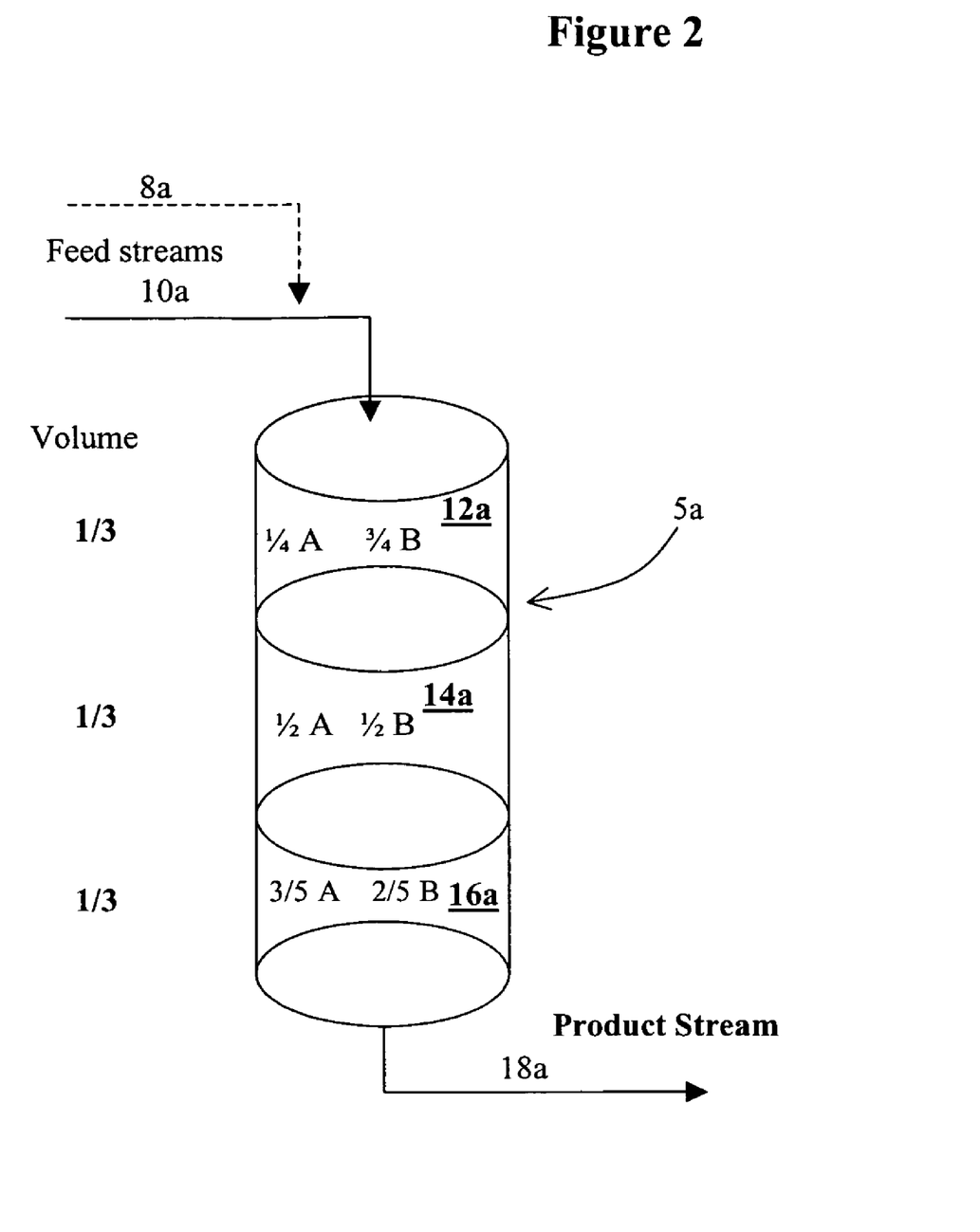
FIG. 2 is a perspective view of a catalyst bed containing a catalyst blend that is used to selectively produce a mercaptan, such as 1-propanethiol (normal propyl mercaptan), from a corresponding alcohol in one process step in accordance with an embodiment of the present invention.
Figure 3:
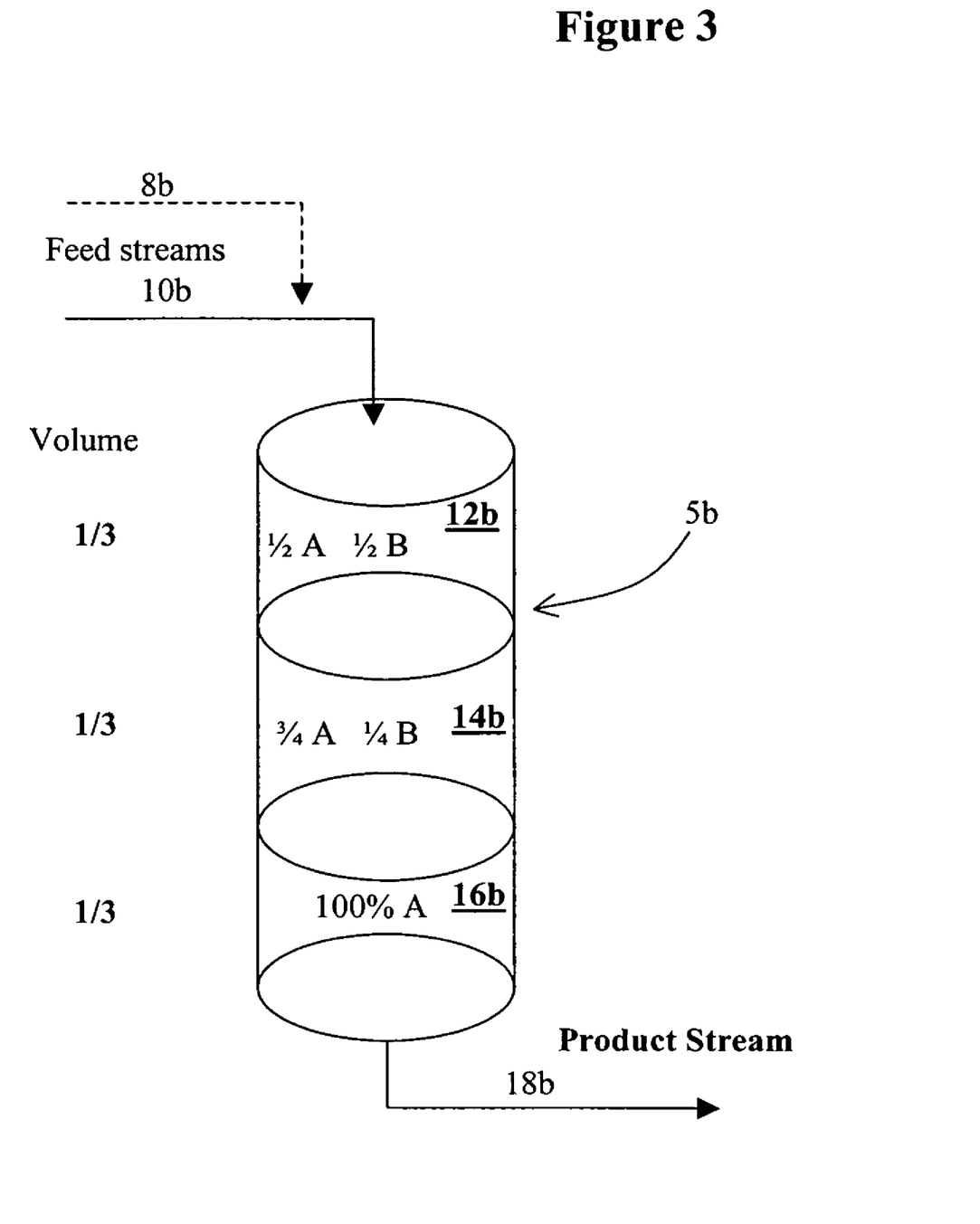
FIG. 3 is a perspective view of a catalyst bed containing a catalyst blend that is used to selectively produce a mercaptan, such as 1-butanethiol (normal butyl mercaptan), from a corresponding alcohol in one process step in accordance with an embodiment of the present invention.

In embodiments of the present invention, the catalyst blend 5 includes a plurality of zones, 12, 14, 16. Each zone has a lower volumetric ratio of the dehydrating catalyst B to the hydrotreating catalyst A than the previous zone. As shown in FIGS. 1-3, the volumetric ratio of the hydrotreating catalyst A to the dehydrating catalyst B increases from a first zone 12 to a middle zone 14 to a last zone 16. As used herein, the term "zone" describes sections of a reactor that contain a different concentration of catalyst blend components than a previous section of the reactor. Zones typically do not have a physical barrier to separate each zone. A physical barrier can be used to separate each zone, if desired. For example, a separate reactor vessel can be used to separate each zone. When there is not a physical barrier present, eventually the different concentrations in each of the zones will intermingle to become a continuum along the reactor vessel.

Although only three zones are shown in FIGS. 1-3 and are described herein, any number of zones can be used to form the catalyst blend 5. In an aspect, each zone contains a lower volumetric ratio of the dehydrating catalyst B to the hydrotreating catalyst A than the prior zone. In some embodiments, the last zone 16 within the catalyst blend 5 can contain only the hydrotreating catalyst A. In aspect, each zone can have an equal of material contained therein. In another aspect, the zones can have varying volumes of material contained therein.

Catalysts suitable for use in this invention as the hydrotreating catalyst A include at least one Group IIIA-VIIIA transition metal and a support. Some suitable catalysts for use as the hydrotreating catalyst A are known as sulfactive hydrogenation catalysts or hydrodesulfurization (HDS) catalysts. The hydrotreating catalyst A can include the oxides of Group VIA and Group VIIIA metals such as, but not limited to, cobalt, nickel, molybdenum, iron, tungsten, chromium, and platinum. Alternatively, the hydrotreating catalyst A can include the sulfides of Group VIA and Group VIIIA metals such as, but not limited to, cobalt, nickel, molybdenum, iron, tungsten, chromium, and platinum. In yet other embodiments, the hydrotreating catalyst A can include the oxides, sulfides, or mixtures thereof, of Group VIA and Group VIIIA metals such as, but not limited to, cobalt, nickel, molybdenum, iron, tungsten, chromium, and platinum. In some embodiments, the hydrotreating catalyst A comprises molybdenum. In some embodiments, the hydrotreating catalyst A includes two transition metals. In particular embodiments, the hydrotreating catalyst A includes cobalt and molybdenum. In other embodiments, the hydrotreating catalyst A includes nickel and molybdenum. Some suitable catalysts are available from catalyst manufacturers such as Criterion, Engelhard, Haldor-Topsoe, Akzo, and Chevron.

Supports suitable for use as a carrier for the transition metal component of the hydrotreating catalyst A include any material that is inert to the reaction conditions. Some suitable supports include activated carbon, alumina, zirconia, thoria, pumice, silica, and silica-alumina. In some embodiments, the support is alumina. In other embodiments, the support is a gamma (γ)-alumina. Generally, the support comprises from 50 to 90 percent by weight of the catalyst composition. Alternatively, the support can comprise from 50 to 70 percent by weight of the catalyst composition; alternatively, from 60 to 85 percent by weight of the catalyst composition; or alternatively, from 70 to 80 percent by weight of the catalyst composition.

Sulfactive hydrogenation catalysts or hydrodesulfurization catalysts comprising at least one Group IIIA-VIIIA transition metal and a support are commercially available. In some embodiments, the hydrotreating catalyst A comprises a Group IIIA-VIIIA transition metal oxide, a Group IIIA-VIIIA transition metal sulfide, or mixture thereof and a support. Typically, the hydrotreating catalyst A can be available in the form of a metal oxide and a support. In some embodiments, the hydrotreating catalyst A is partially or completely sulfided prior to use. Alternatively, the hydrotreating catalyst A can be employed directly in the oxide form because sulfiding occurs in the presence of $H_2S$ under the reaction conditions.

Generally, the hydrotreating catalyst A comprises an oxide of molybdenum and a support. In some embodiments, the hydrotreating catalyst A comprises an oxide, sulfide, or mixed oxide/sulfide of molybdenum. In other embodiments, the hydrotreating catalyst A comprises an oxide of molybdenum supported on alumina. Typically, the oxide of molybdenum is $MoO_3$. However, other oxides, sulfides or mixed oxides/sulfides of molybdenum can be used. Additionally, other molybdenum compounds, including oxides, sulfides, or mixed oxides/sulfides of molybdenum, which can be converted to $MoO_3$ upon oxidation in oxygen can also be used. While the applicable quantities of the oxide of molybdenum present in the catalyst are stated as weight percent of $MoO_3$, one skilled in the art will recognize that the applicable compositions include other molybdenum materials and the quantities of molybdenum materials that, upon oxidation, will yield the disclosed quantities of $MoO_3$ described herein. Typically, the hydrotreating catalyst A comprises from 5 to 40 weight percent of an oxide of molybdenum; alternatively, from 8 to 35 weight percent; alternatively, from 8 to 15 weight percent; alternatively, from 10 to 20 weight percent; or alternatively, from 15 to 30 weight percent.

In some embodiments, the hydrotreating catalyst A comprises an oxide of cobalt, an oxide of molybdenum, and a support. In other embodiments, the hydrotreating catalyst A comprises an oxide of cobalt and an oxide of molybdenum supported on alumina. The oxide of molybdenum and the support have been described herein and are generally applicable to the catalyst compositions comprising an oxide of cobalt, an oxide of molybdenum, and a support. Some suitable commercially available catalysts are commonly referred to as cobalt molybdate on alumina. Typically, the oxide of cobalt is CoO. However, other cobalt compounds, including oxides, sulfides, or mixed oxides and sulfides of cobalt, which can be converted to CoO upon oxidation in oxygen can also be used. While the applicable quantities of the oxide of cobalt present in the catalyst are stated as weight percent of CoO, one skilled in the art will recognize that the applicable compositions includes other cobalt materials and the quantities of cobalt materials which upon oxidation will yield the disclosed quantities of CoO described herein.

In some embodiments, the hydrotreating catalyst A comprising an oxide of cobalt, an oxide of molybdenum, and a support can comprise from 1 to 10 weight percent of an oxide of cobalt. In other embodiments, the hydrotreating catalyst A comprising an oxide of cobalt, an oxide of molybdenum, and a support can comprise from 2 to 7 weight percent of an oxide of cobalt; or alternatively, from 3 to 5 weight percent of an oxide of cobalt. In some embodiments, the hydrotreating catalyst A comprising an oxide of cobalt, an oxide of molybdenum, and a support comprises from 8 to 35 weight percent $MoO_3$, from 1 to 10 weight percent CoO, and from 50 to 91 percent alumina; alternatively, from 10 to 20 weight percent $MoO_3$, from about 3 to 5 weight percent CoO, and from 75 to 87 percent alumina; or alternatively, from 15 to 30 weight percent $MoO_3$, from 3 to 5 weight percent CoO, and from 65 to 82 percent alumina. In further embodiments, the hydrotreating catalyst A can also contain from 0.05 to 1 weight percent $Na_2O$. In other embodiments, the hydrotreating catalyst A can also contain up to 0.05 weight percent iron. In the embodiment wherein the hydrotreating catalyst A also contains iron, the iron can be present as elemental iron or as an oxide.

In some embodiments, the hydrotreating catalyst A comprises an oxide of nickel, an oxide of molybdenum, and a support. In other embodiments, the hydrotreating catalyst A comprises oxides of nickel and an oxide of molybdenum supported on alumina. The oxide of molybdenum and the support have been described herein and are generally applicable to the catalysts comprising an oxide of nickel, an oxide of molybdenum, and a support described herein. Typically, the oxide of nickel is NiO. However, other nickel compounds, including oxides, sulfides, or mixed oxides and sulfides of nickel, which can be converted to NiO upon oxidation in oxygen can also be used. While the applicable quantities of the oxide of nickel present in the hydrotreating catalyst A are stated as weight percent of NiO, one skilled in the art will recognize that the applicable compositions include other nickel materials and the quantities of nickel materials that, upon oxidation, will yield the disclosed quantities of NiO described herein.

In some embodiments, the catalyst comprising an oxide of nickel, an oxide of molybdenum, and a support can comprise from 0.5 to 10 weight percent of an oxide of nickel. In other embodiments, the catalyst comprising an oxide of nickel, an oxide of molybdenum, and a support can comprise from 1 to 7 weight percent of an oxide of nickel; or alternatively, from 2 to 5 weight percent of an oxide of nickel. In other embodiments, the catalyst comprising an oxide of nickel, an oxide of molybdenum, and a support comprises from 8 to 35 weight percent $MoO_3$, from 0.5 to 10 weight percent NiO, and from 55 to 91.5 percent alumina; alternatively, from 8 to 35 weight percent $MoO_3$, from 1 to 7 weight percent NiO, and from 58 to 91 percent alumina; alternatively, from 15 to 30 weight percent $MoO_3$, from 2 to 5 weight percent NiO, and from 65 to 83 percent alumina; alternatively, from 10 to 20 weight percent $MoO_3$, from 2 to 5 weight percent NiO, and from 75 to 88 percent alumina; or alternatively, from 8 to 15 weight percent $MoO_3$, from 2 to 5 weight percent NiO, and from 80 to 90 percent alumina. In further embodiments, the catalyst can also contain from 0.05 to 1 weight percent $Na_2O$. In yet other embodiments, the catalyst can also contain up to 0.05 weight percent iron. In the embodiment wherein the catalyst also contains iron, the iron can be present as elemental iron or as an oxide.

In an aspect, the dehydration catalyst B comprises gamma (γ)-alumina. In another aspect, the alcohol feed stream 8 can have between two and twenty carbon atoms. Example alcohols that can be used in embodiments of the present invention that use gamma (γ)-alumina as the dehydration catalyst B include methanol, ethanol, 1-propanol, 2-propanol, cyclohexanol, 1-butanol, 2-butanol, or combinations thereof. The alcohol feed stream 8 is reacted with the sulfur compound reactant stream 10, in the presence of the catalyst blend 5, to produce the corresponding mercaptan or sulfide product stream 18. The sulfur compound reactant stream 10 can include hydrogen sulfide, methanethiol (methyl mercaptan), ethanethiol (ethyl mercaptan), or combinations thereof. The mercaptan or sulfide product stream 18 can include ethanethiol (ethyl mercaptan), 2-propanethiol (isopropyl mercaptan), cyclohexanethiol (cyclohexyl mercaptan), 2-butanethiol (secondary butyl mercaptan), 2-thiopropane (dimethyl sulfide), 1-(methylthio)ethane (methyl ethyl sulfide), 1,1'-thiobisethane (diethyl sulfide), or combinations thereof, depending upon the selected sulfur compound reactant stream 10 and the selected alcohol feed stream 8.

In some embodiments, the alcohol feed stream 8 can be a primary or normal alcohol. In other embodiments, the alcohol feed stream 8 can be a secondary alcohol. For example, the alcohol feed stream 8 can be cyclohexanol, which produces cyclohexanethiol (cyclohexyl mercaptan). Other suitable alcohols will be apparent to those of ordinary skill in the art and are to be considered within the scope of the present invention.

In addition to producing mono or single thiol group containing mercaptans, dimercaptans, which contain at least two thiol groups, can also be produced using the methods described herein. For example, 1,6-hexanediol can be fed as the alcohol feed stream 8 and reacted with the sulfur compound reactant stream 10, i.e. hydrogen sulfide, to produce 1,6-hexanedithiol (1,6-dimercaptohexane) in the product stream 18.

In embodiments of the present invention, the molar feed rate of the sulfur compound reactant stream 10 to the alcohol feed stream 8 at which the feedstocks are sent to the catalyst blend 5 can be changed, depending upon the alcohol that is being fed, the conversion of the alcohol desired, and other operating parameters. For example, for most embodiments, the preselected sulfur compound reactant to alcohol molar feed ratio can range from about 9:1 to about 20:1. In some aspects, the molar feed ratio can be about 12:1, such as to produce 1-butanethiol (n-butyl mercaptan) or 1-propanethiol (n-propyl mercaptan). In some aspects, the molar feed ratio can be in a range of about 10:1 to about 20:1, such as to produce 2-butyloctanethiol. More sulfur compound reactant stream 10 can always be supplied, however, the excess sulfur compound reactant will likely not react with the alcohol feed stream 8.

Besides the molar feed ratio of the feedstock chemicals, other process parameters can be varied in embodiments of the present invention. For example, the catalyst blend 5 can be operated at a preselected temperature that can be varied in a range of about 220° C. to about 250° C.; or alternatively, from about 230° C. to about 240° C. As another example, the catalyst blend 5 can be operated at a preselected pressure that can be varied in a range of about 450 psig to about 600 psig.

As shown in FIG. 3, a process for the selective production of a mercaptan or a sulfide product stream 18b from an alcohol feed stream 8b is advantageously provided as another embodiment of the present invention. This process includes the step of contacting the alcohol feed stream 8b, in the presence of a catalyst blend 5b, with a sulfur compound reactant stream 10b to produce the mercaptan or the sulfide stream 10b in one-pass.

To produce a sulfide, the sulfur compound reactant stream 10b can be a mercaptan, such as methanethiol (methyl mercaptan) or ethanethiol (ethyl mercaptan). Either one of these mercaptans can be reacted with methanol or ethanol as the alcohol feed stream 8b to produce 2-thiopropane (dimethyl sulfide), 1-(methylthio)ethane (methyl ethyl sulfide), or 1,1'-thiobisethane (diethyl sulfide), depending upon the selected sulfur compound reactant stream 10b and alcohol feed stream 8b. For example, methanethiol (methyl mercaptan) can be reacted with methanol, in the presence of the catalyst blend 5b of the present invention, to produce 2-thiopropane (dimethyl sulfide) or with ethanol to produce 1-(methylthio)ethane (methyl ethyl sulfide). As another example, ethanethiol (ethyl mercaptan) can be reacted with methanol to produce 1-(methylthio)ethane (methyl ethyl sulfide) or with ethanol to produce 1,1'-thiobisethane (diethyl sulfide). As shown in FIG. 3, the catalyst blend 5b includes a plurality of zones with each zone having a lower volumetric ratio of the alumina diluent B to the hydrotreating catalyst A than the previous zone.

In some aspects, the catalyst blend comprises a hydrotreating catalyst A and an alumina diluent B. The hydrotreating catalyst A can be any hydrotreating catalyst previously described herein. The alumina diluent B comprises alpha ($\alpha$)-alumina. In embodiments of the present invention, the alcohol feed stream 8b can have between two and twenty carbon atoms. Example alcohols that can be used in embodiments of the present invention that use alpha ($\alpha$)-alumina as the alumina diluent B include methanol, 1-ethanol, 1-propanol, 2-propanol, cyclohexanol, phenol, 1-butanol, 2-butanol, 2-butyl-1-octanol, $\alpha$-hydroxytoluene, 1,6-hexanediol, 1-phenyl-1-ethanol, 2-phenyl-1-ethanol, or combinations thereof. The alcohol feed stream 8 is reacted with the sulfur compound reactant stream 10b, in the presence of the catalyst blend 5, to produce the corresponding mercaptan or sulfide stream 18b. The sulfur compound reactant stream 10b can include hydrogen sulfide, methanethiol (methyl mercaptan), ethanethiol (ethyl mercaptan), or combinations thereof. The mercaptan or sulfide product stream 18 can include methanethiol (methyl mercaptan), ethanethiol (ethyl mercaptan), 1-propanethiol (normal propyl mercaptan), 2-propanethiol (isopropyl mercaptan), cyclohexanethiol (cyclohexyl mercaptan), 1-butanethiol (normal butyl mercaptan), 2-butanethiol (secondary butyl mercaptan), 2-butyloctanethiol, benzenethiol (thiophenol or phenyl mercaptan), $\alpha$-toluenethiol (benzyl mercaptan), 1,6-hexanedithiol (1,6-dimercaptohexane), 1-phenyl-1-ethanethiol, 2-phenyl-1-ethanethiol, 2-thiopropane (dimethyl sulfide), 1-(methylthio)ethane (methyl ethyl sulfide), 1,1'-thiobisethane diethyl sulfide), or combinations thereof, depending upon the selected sulfur compound reactant stream 10b and the selected alcohol feed stream 8b.

In some embodiments, the alcohol feed stream 8 and the sulfur compound reactant stream 10 are reacted under near isothermal conditions. The reaction of the alcohol feed stream 8 with the sulfur compound reactant stream 10 in the presence of the hydrotreating catalyst A is an exothermic reaction. The presence of the alumina diluent B dilutes the concentration of the hydrotreating catalyst A across the catalyst blend 5b. In the first zone 12, greater than or equal to amounts of the alumina diluent B are present than the hydrotreating catalyst A. The alumina diluent B reduces rate of the enthalpy released by the exothermic reaction that occurs in the presence of the hydrotreating catalyst A. By using both the hydrotreating catalyst A and the alumina diluent B, near isothermal reaction conditions can be maintained along the catalyst blend 5.

As in other embodiments of the present invention, the volumetric ratio of the hydrotreating catalyst A to the alumina diluent B can be varied, depending upon the feed streams and products produced. In an aspect, the volumetric ratio of the hydrotreating catalyst A to the alumina diluent B increases from an inlet of the diluted catalyst blend 5 to an outlet of the diluted catalyst blend 5.

The present invention also includes a process for selective production of a mercaptan or a sulfide using a catalyst blend 5 having a volumetric ratio of the hydrotreating catalyst A to the dehydration catalyst B or the alumina diluent B that increases from a reactor vessel inlet to a reactor vessel outlet in order to maintain near isothermal conditions during reaction of the alcohol feed stream 8 and the sulfur compound reactant stream 10, as shown in FIGS. 1-3.

In an aspect, the catalyst blend 5 comprises about 40% by volume to about 95% by volume hydrotreating catalyst A and about 5% by volume to about 60% by volume dehydrating catalyst or alumina diluent B. The hydrotreating catalyst A can be any hydrotreating catalyst described herein. The dehydrating catalyst B can comprise gamma ($\gamma$)-alumina. The alumina diluent B can comprise alpha ($\alpha$)-alumina.

As shown in FIGS. 1-3, the catalyst blend 5 is typically contained within three zones, the first zone 12, the middle zone 14, and the last zone 16. In some aspects, the volumetric ratio of the dehydration catalyst or diluent to the hydrotreating catalyst in the first zone 12 is in a range of about 1:0.75 to about 1:3.25, the volumetric ratio of the dehydration catalyst or diluent to the hydrotreating catalyst in the middle zone 14 is in a range of about 4:1 to about 1.25:1, and the volumetric ratio of the dehydration catalyst or diluent to the hydrotreating catalyst in the last zone 16 is in a range of about 1:0 to about 3:2.

In the embodiment shown in FIG. 1, the first zone 12 has ⅓ by volume of the hydrotreating catalyst A and about ⅔ by volume of the dehydration catalyst B, which can also be described as a volumetric ratio of about 1:2. The middle zone 14 has about ½ by volume of the hydrotreating catalyst A and about ½ by volume of the dehydration catalyst B, which corresponds to the volumetric ratio of about 1:1. The last zone 16 has the hydrotreating catalyst A, which corresponds to the volumetric ratio of 1:0. In an aspect, the catalyst blend 5 shown in FIG. 1 can be used to produce cyclohexanethiol (cyclohexyl mercaptan) or ethanethiol (ethyl mercaptan).

In embodiments of the present invention that use normal butanol as the alcohol feed stream 8b, as shown in FIG. 3, the first zone 12b has ½ by volume of the hydrotreating catalyst A and about ½ by volume of the alumina diluent B, which corresponds to the volumetric ratio of about 1:1. The middle zone 14b has about ¾ by volume of the hydrotreating catalyst A and about ¼ by volume of the alumina diluent B, which corresponds to the volumetric ratio of about 3:1. The last zone 16b has the hydrotreating catalyst A, which corresponds to the volumetric ratio of 1:0. The catalyst blend 5b can be used to produce 1-butanethiol (normal butyl mercaptan) by reacting normal butanol and hydrogen sulfide in the presence of the catalyst blend 5b.

FIG. 2 illustrates an embodiment of the present invention that uses normal propanol as the alcohol feed stream 8a to produce the mercaptan product stream 18a. The catalyst blend 5a includes the first zone 12a that has ¾ by volume of the hydrotreating catalyst A and about ¼ by volume of the alumina diluent B, which corresponds to the volumetric ratio of about 1:3. The middle zone 14a has about ½ by volume of the hydrotreating catalyst A and about ½ by volume of the alumina diluent B, which corresponds to the volumetric ratio of about 1:1. The last zone 16a has about ⅗ of the hydrotreating catalyst A and about ⅖ of the alumina diluent B, which corresponds to the volumetric ratio of about 3:2. The catalyst blend 5a can be used to produce 1-propanethiol (normal propyl mercaptan) by reacting the normal propanol feed stream 8a and the hydrogen sulfide reactant stream 10a in the presence of the catalyst blend 5a.

The processes described herein allow a lower cost feedstock to be used to produce mercaptans or sulfides than with prior art processes. The conversion rates of the alcohols that are used to produce mercaptans or sulfides are high, which reduces the need to separate the products, when compared with prior attempts to produce mercaptans or sulfides from alcohols using solid acid catalysts.

While the invention has been shown or described in only some of its forms, it should be apparent to those skilled in the art that it is not so limited, but is susceptible to various changes without departing from the scope of the invention.

For example, various means of controlling the hydrogen sulfide to alcohol molar feed ratio can be used. The catalyst blend can be placed in a single vessel or separate vessels including one or more of the zones in each vessel. Other variations will be apparent to those of ordinary skill in the art and are to be considered within the scope of the present invention.

EXAMPLES

Example 1

Conversion of Ethanol to Ethanethiol (Ethyl Mercaptan)

As shown in FIG. 1, ethanol (alcohol feed stream 8) was converted to ethenethiol (ethyl mercaptan) (mercaptan stream 18) by reacting ethanol with hydrogen sulfide (sulfur compound reactant stream 10), in the presence of the catalyst blend 5 described herein. 1,1'-Thiobisethane (diethyl sulfide) was another product that was formed during production of ethenethiol (ethyl mercaptan) from methanol. Both reactions were exothermic, as indicated in the following two reactions.

$C_2H_5OH+H_2S \rightarrow C_2H_5SH+H_2O$ $\Delta H_{rxn}=-26600$ BTU/lbmole $C_2H_5OH+C_2H_5SH \rightarrow C_2H_5SC_2H_5+H_2O$ $\Delta H_{rxn}=-23500$ BTU/lbmole The catalyst blend that was used in this example was a blend of gamma (γ)-alumina (dehydration catalyst) B and CoMo/alumina (hydrotreating catalyst) A. The dehydration catalyst B used was produced by Norton Chemical Process and Products and is available commercially as SA6176. The hydrotreating catalyst A was produced by Haldor Topsoe Inc. and is available commercially as TK-554. The ethenethiol (ethyl mercaptan) was produced in a fixed bed catalytic flow reactor in a downflow formation.

The catalyst packing scheme used had three equal zones by volume, as shown in FIG. 1. The first zone 12 was filled with ⅔ by volume of the gamma (γ)-alumina catalyst B and ⅓ by volume of the CoMo/alumina hydrotreating catalyst A. The middle zone 14 was filled with ½ of each of the gamma (γ)-alumina catalyst B and the CoMo/alumina hydrotreating catalyst A. The last zone was filled with all CoMo/alumina hydrotreating catalyst A. The results achieved with such a catalyst bed configuration are included in Table 1.

TABLE 1

Ethanethiol (Ethyl Mercaptan) (EtSH) Synthesis Results

| | | | | | | | | | | | | | | Product Compositions | | |
|---|---|---|---|---|---|---|---|---|---|---|---|---|---|---|---|---|
| | | | | Feed Properties and Conditions | | | | | | | | | | | | |
| Run Number | Feedrate cc/min | Ethanol grams | $H_2S$ grams | Press psig | L/D | Total CoMo cat g | catvol cc | Total γ-alumina g | WHSV | $H_2S$/ethanol molar feed ratio | WAT °C. | WAT °F. | Ethanol wt % | EtSH wt % | lights wt % | heavies wt % |
| 1 | 3.4 | 140 | 936 | 450 | 22 | 55 | 114 | 27.2 | 0.23 | 12.2 | 195 | 383 | 18.91 | 19.68 | 4.17 | 57.24 |
| 2 | 3.4 | 140 | 936 | 450 | 22 | 55 | 114 | 27.2 | 0.23 | 12.2 | 200 | 392 | 50.75 | 32.22 | 0.87 | 16.17 |

TABLE 1-continued

Ethanethiol (Ethyl Mercaptan) (EtSH) Synthesis Results

| | Feed Properties and Conditions | | | | | | | | | | | | Product Compositions | | | |
|---|---|---|---|---|---|---|---|---|---|---|---|---|---|---|---|---|
| Run Number | Feed-rate cc/min | Ethanol grams | $H_2S$ grams | Press psig | L/D | Total CoMo cat g | catvol cc | Total γ-alumina g | WHSV | $H_2S$/ethanol molar feed ratio | WAT °C. | WAT °F. | Ethanol wt % | EtSH wt % | lights wt % | heavies wt % |
| 3 | 3.4 | 140 | 936 | 450 | 22 | 55 | 114 | 27.2 | 0.23 | 12.2 | 200 | 392 | 0.76 | 34.84 | 34.84 | 12.21 |
| 4 | 3.4 | 140 | 936 | 450 | 22 | 55 | 114 | 27.2 | 0.23 | 12.2 | 210 | 410 | 0.68 | 37.69 | 37.69 | 13.87 |
| 5 | 3.4 | 140 | 936 | 450 | 22 | 55 | 114 | 27.2 | 0.23 | 12.2 | 210 | 410 | 23.10 | 62.23 | 2.09 | 15.65 |
| 6 | 3.4 | 140 | 936 | 450 | 22 | 55 | 114 | 27.2 | 0.23 | 12.2 | 215 | 419 | 25.47 | 32.50 | 3.39 | 9.94 |
| 7 | 3.4 | 140 | 936 | 450 | 22 | 55 | 114 | 27.2 | 0.23 | 12.2 | 218 | 424 | 33.83 | 35.21 | 4.49 | 10.97 |
| 8 | 3.4 | 140 | 936 | 450 | 22 | 55 | 114 | 27.2 | 0.23 | 12.2 | 225 | 436 | 24.50 | 58.51 | 1.80 | 6.99 |
| 9 | 3.4 | 140 | 936 | 450 | 22 | 55 | 114 | 27.2 | 0.23 | 12.2 | 225 | 437 | 10.15 | 67.95 | 3.28 | 20.08 |
| 10 | 3.4 | 140 | 936 | 450 | 22 | 55 | 114 | 27.2 | 0.23 | 12.2 | 225 | 437 | 9.21 | 62.25 | 1.21 | 27.87 |
| 11 | 3.4 | 113 | 928 | 450 | 22 | 55 | 114 | 27.2 | 0.19 | 15 | 193 | 379 | 27.32 | 30.98 | 2.32 | 39.38 |
| 12 | 3.4 | 113 | 928 | 450 | 22 | 84 | 114 | 27.2 | 0.19 | 15 | 193 | 379 | 57.61 | 42.39 | 0.00 | |
| 13 | 3.4 | 113 | 928 | 450 | 22 | 84 | 114 | 27.2 | 0.19 | 15 | 193 | 379 | 61.47 | 38.53 | 0.00 | |
| 14 | 3.4 | 113 | 928 | 450 | 22 | 84 | 114 | 27.2 | 0.19 | 15 | 196 | 384 | 55.66 | 37.20 | 0.00 | 7.14 |
| 15 | 3.4 | 113 | 928 | 450 | 22 | 84 | 114 | 27.2 | 0.19 | 15 | 197 | 386 | 44.96 | 47.09 | 0.00 | 7.95 |
| 16 | 3.4 | 113 | 928 | 450 | 22 | 84 | 114 | 27.2 | 0.19 | 15 | 198 | 388 | 32.33 | 62.32 | 0.00 | 5.35 |
| 17 | 3.4 | 113 | 928 | 450 | 22 | 84 | 114 | 27.2 | 0.19 | 15 | 205 | 401 | 36.45 | 51.85 | 0.00 | 11.70 |
| 18 | 3.4 | 113 | 928 | 450 | 22 | 84 | 114 | 27.2 | 0.19 | 15 | 205 | 401 | 18.96 | 68.95 | 0.00 | 12.09 |
| 19 | 3.4 | 113 | 928 | 450 | 22 | 84 | 114 | 27.2 | 0.19 | 15 | 205 | 401 | 23.41 | 61.69 | 0.00 | 14.90 |
| 20 | 3.4 | 113 | 928 | 450 | 22 | 84 | 114 | 27.2 | 0.19 | 15 | 210 | 410 | 16.41 | 67.82 | 0.00 | 15.77 |
| 21 | 3.4 | 113 | 928 | 450 | 22 | 84 | 114 | 27.2 | 0.19 | 15 | 212 | 413 | 11.48 | 71.02 | 0.00 | 17.10 |
| 22 | 3.4 | 101 | 1112 | 500 | 22 | 54.5 | 114 | 27.2 | 0.15 | 20 | 225 | 437 | 5.04 | 77.10 | 0.00 | 17.86 |
| 23 | 3.4 | 101 | 1112 | 500 | 22 | 54.5 | 114 | 27.2 | 0.15 | 20 | 230 | 446 | 3.42 | 80.24 | 0.00 | 16.34 |
| 24 | 3.4 | 101 | 1112 | 500 | 22 | 54.5 | 114 | 27.2 | 0.15 | 20 | 230 | 446 | 2.73 | 76.28 | 0.00 | 18.99 |
| 25 | 3.4 | 101 | 1112 | 500 | 22 | 54.5 | 114 | 27.2 | 0.15 | 20 | 240 | 464 | 2.57 | 76.88 | 0.00 | 18.55 |
| 26 | 3.4 | 101 | 1112 | 500 | 22 | 54.5 | 114 | 27.2 | 0.15 | 20 | 240 | 464 | 0.80 | 81.65 | 0.00 | 17.55 |
| 27 | 3.4 | 101 | 1112 | 500 | 22 | 54.5 | 114 | 27.2 | 0.15 | 20 | 240 | 464 | 0.00 | 92.27 | 0.00 | 7.73 |
| 28 | 3.4 | 101 | 1112 | 500 | 22 | 54.5 | 114 | 27.2 | 0.15 | 20 | 250 | 482 | 0.00 | 81.18 | 0.67 | 18.15 |
| 29 | 3.4 | 101 | 1112 | 500 | 22 | 54.5 | 114 | 27.2 | 0.15 | 20 | 250 | 482 | 0.00 | 80.76 | 0.00 | 19.24 |
| 30 | 3.4 | 101 | 1112 | 500 | 22 | 54.5 | 114 | 27.2 | 0.15 | 20 | 250 | 482 | 0.00 | 88.62 | 0.38 | 11.38 |
| 31 | 3.4 | 101 | 1112 | 500 | 22 | 54.5 | 114 | 27.2 | 0.15 | 20 | 250 | 482 | 0.00 | 80.87 | 0.79 | 18.34 |
| 32 | 3.4 | 101 | 1112 | 500 | 22 | 54.5 | 114 | 27.2 | 0.15 | 20 | 250 | 482 | 0.00 | 82.39 | 0.98 | 16.63 |

Based upon the results achieved with using the described catalyst blend loading, a weight average bed temperature (WAT) of 225-245° C. was the optimal temperature range. As used herein, the term weight average bed temperature is the average of the temperatures measured across the reactor bed: $(T_1+T_2+\ldots+T_n)/n$. As an example, the weight average bed temperature for a reactor where the temperature is measured only at the reactor bed inlet and the reactor bed outlet is $(T_{outlet}+T_{inlet})/2$.

It appears as if a temperature of at least 240° C. was optimal for 100% ethanol conversion. At temperatures greater than 245° C., greater heavies formation resulted. A pre-heat temperature of approximately 180° C. was used and was beneficial. A beneficial pressure range was in a range of about 450 to about 600 psig. An ethanol weight hourly space velocity (WHSV) of about 0.15 gr. liq./hr./gr. cat. to about 0.23 gr. liq./hr./gr. cat. was used. In an aspect, the ethanol WHSV ranges from about 0.15 to about 0.50 gr. liq./hr./gr. cat. In some embodiments, the hydrogen sulfide to methanol molar feed ratio was 15:1 or greater. It is believed that the lights primarily contain ethylene and the heavies primarily contain 1,1'-thiobisethane (diethyl sulfide). The lights can also include carbon monoxide, methane, ethane, and other gaseous, low molecular weight compounds. All weight percents contained in Table 1 are on a water free basis. As shown by the synthesis reactions for ethenethiol (ethyl mercaptan), one mole of water is produced for every mole of ethanol consumed. Essentially no unreacted ethanol was in many of the runs that produced the mercaptan. In some embodiments, however, the amount of unreacted ethanol was less than about 10 wt. %.

Example 2

Conversion of Normal Propanol to 1-Propanethiol (n-Propyl Mercaptan)

Normal propanol (alcohol feed stream) 8a was converted to 1-propanethiol (n-propyl mercaptan) (mercaptan stream) 18a in a fixed bed catalytic flow reactor in downflow using the following exothermic reactions:

n-$C_3H_7OH+H_2S \rightarrow$ n-$C_3H_7SH+H_2O$ $\Delta H_{rxn}=-26900$ BTU/lbmole.

n-$C_3H_7OH+$n-$C_3H_7SH \rightarrow H_7C_3SC_3H_7+H_2O$ $\Delta H_{rxn}=$ $-22900$ BTU/lbmole.

The catalyst that was used in this example was a catalyst blend 5a of a CoMo/alumina (hydrotreating catalyst) A and an alpha (α)-alumina (dehydrating catalyst) B, as shown in FIG. 2. The hydrotreating catalyst A was produced by Haldor Topsoe Inc. and is commercially available as TK-554. The dehydrating catalyst B was produced by Norton Chemical Process and Products and is available commercially as 14 grit Alundum. The catalyst blend 5a was pre-sulfided in place prior to the reactants being fed to the catalyst blend 5a.

The catalyst blend 5a was packed in the reactor in three equal zones by volume. The first zone 12a contained 25% of the hydrotreating catalyst A and 75% of the dehydrating catalyst B. The middle zone 14a contained 50% of each of the hydrotreating and dehydrating catalysts A, B. The last zone 16 contained 60% or ⅗ of the hydrotreating catalyst A and 40% or ⅖ of the dehydrating catalyst B. The results of the synthesis of 1-propanethiol (n-propyl mercaptan) using this particular catalyst blend are included in Table 2.

TABLE 2

1-Propanethiol (n-Propyl Mercaptan) (NPM) Synthesis Results

| | Feed Properties and Conditions | | | | | | | | | | | Product Compositions | | | |
|---|---|---|---|---|---|---|---|---|---|---|---|---|---|---|---|
| Run Number | Feedrate cc/mm | nPropanol grams | $H_2S$ grams | Press psig | L/D | Total CoMo Cat, g | Catvol cc | WHSV | $H_2S$/nPropanol molar feed ratio | WAT Temp °C. | WAT Temp °F. | nPropanol Area % | NPM Area % | Lights Area % | Heavies Area % |
| 1 | 3.2 | 141 | 812 | 500 | 22 | 42 | 149 | 0.67 | 10.2 | 180 | 356 | 72.3 | 6.6 | 0.0 | 21.2 |
| 2 | 3.2 | 141 | 812 | 500 | 22 | 42 | 149 | 0.67 | 10.2 | 180 | 356 | 82.7 | 7.0 | 0.0 | 10.3 |
| 3 | 3.2 | 141 | 812 | 500 | 22 | 42 | 149 | 0.67 | 10.2 | 200 | 392 | 71.7 | 17.2 | 0.0 | 11.1 |
| 4 | 3.2 | 141 | 812 | 500 | 22 | 42 | 149 | 0.67 | 10.2 | 200 | 392 | 52.6 | 36.1 | 0.0 | 11.3 |
| 5 | 3.2 | 141 | 812 | 500 | 22 | 42 | 149 | 0.67 | 10.2 | 220 | 428 | 49.1 | 35.2 | 0.0 | 15.7 |
| 6 | 3.2 | 141 | 812 | 500 | 22 | 42 | 149 | 0.67 | 10.2 | 220 | 424 | 31.8 | 51.3 | 0.0 | 16.9 |
| 7 | 3.2 | 141 | 812 | 500 | 22 | 42 | 149 | 0.67 | 10.2 | 220 | 428 | 31.6 | 50.7 | 0.0 | 17.8 |
| 8 | 3.3 | 139.5 | 812 | 450 | 22 | 42 | 149 | 0.69 | 10.3 | 180 | 356 | 91.8 | 4.1 | 0.0 | 4.1 |
| 9 | 3.3 | 139.5 | 812 | 450 | 22 | 42 | 149 | 0.69 | 10.3 | 180 | 356 | 89.3 | 8.7 | 0.0 | 2.0 |
| 10 | 3.3 | 139.5 | 812 | 450 | 22 | 42 | 149 | 0.69 | 10.3 | 180 | 356 | 91.1 | 6.0 | 0.0 | 3.0 |
| 11 | 3.3 | 139.5 | 812 | 450 | 22 | 42 | 149 | 0.69 | 10.3 | 180 | 356 | 89.8 | 8.0 | 0.0 | 2.2 |
| 12 | 3.3 | 139.5 | 812 | 450 | 22 | 42 | 149 | 0.69 | 10.3 | 200 | 392 | 83.7 | 12.6 | 0.0 | 3.7 |
| 13 | 3.3 | 139.5 | 812 | 450 | 22 | 42 | 149 | 0.69 | 10.3 | 200 | 424 | 81.0 | 16.1 | 0.0 | 2.9 |
| 14 | 3.3 | 139.5 | 812 | 450 | 22 | 42 | 149 | 0.69 | 10.3 | 200 | 392 | 80.7 | 16.5 | 0.0 | 2.9 |
| 15 | 3.3 | 139.5 | 812 | 450 | 22 | 42 | 149 | 0.69 | 10.3 | 200 | 392 | 80.7 | 15.5 | 0.0 | 3.7 |
| 16 | 3.3 | 140 | 815 | 450 | 22 | 42 | 149 | 0.69 | 10.3 | 220 | 428 | 56.6 | 30.4 | 0.0 | 13.0 |
| 17 | 3.3 | 139.5 | 812 | 450 | 22 | 42 | 149 | 0.69 | 10.3 | 220 | 428 | 55.7 | 40.0 | 0.0 | 4.3 |
| 18 | 3.3 | 139.5 | 812 | 450 | 22 | 42 | 149 | 0.69 | 10.3 | 220 | 428 | 53.4 | 39.0 | 0.0 | 7.6 |
| 19 | 3.3 | 139.5 | 812 | 450 | 22 | 42 | 149 | 0.69 | 10.3 | 220 | 428 | 53.4 | 42.8 | 0.0 | 3.8 |
| 20 | 3.3 | 139.5 | 812 | 450 | 22 | 42 | 149 | 0.69 | 10.3 | 230 | 446 | 39.6 | 54.1 | 0.0 | 6.3 |
| 21 | 3.3 | 139.5 | 812 | 450 | 22 | 42 | 149 | 0.69 | 10.3 | 230 | 424 | 43.1 | 51.1 | 0.8 | 5.0 |
| 22 | 3.3 | 139.5 | 812 | 450 | 22 | 42 | 149 | 0.69 | 10.3 | 230 | 446 | 34.4 | 56.2 | 0.3 | 9.1 |
| 23 | 3.3 | 139.5 | 812 | 450 | 22 | 42 | 149 | 0.69 | 10.3 | 240 | 464 | 34.5 | 58.1 | 0.0 | 7.4 |
| 24 | 3.3 | 139.5 | 812 | 450 | 22 | 42 | 149 | 0.69 | 10.3 | 240 | 464 | 28.3 | 65.5 | 1.9 | 4.3 |

In this example, the optimal process conditions included a weight average bed temperature (WAT) of at least 240° C. A pre-heat temperature of approximately of 180° C. was used for the synthesis of 1-propanethiol (n-propyl mercaptan) 18. The optimal pressure was in a range of about 450 to 600 psig. The optimal normal propanol weight hourly space velocity (WHSV) was in a range of about 0.67 gr. liq./hr./gr. cat. to about 0.69 gr. liq./hr./gr. cat. In an aspect, the normal propanol WHSV ranges from about 0.25 to about 0.70 gr. liq./hr./gr. cat. In this example, the hydrogen sulfide to normal propanol molar feed ratio was 12:1 or greater.

As shown in Table 2, the best conversion of normal propanol was about 72% of the samples produced. Better conversion of the normal propanol can be achieved using a lower space velocity and a slightly higher temperature. At 240° C., the product composition included less than 1 wt. % lights, 50 wt. % to 60 wt. % 1-propanethiol (n-propyl mercaptan), and 5 wt. % to 10 wt. % heavies, which included primarily 4-thiaheptane (di-n-propyl sulfide). The analysis contained in Table 2 is on a water-free basis. One mole of water was formed for every mole of normal propanol consumed. As shown in Table 2, the lights can also include propylene and carbon monoxide, methane, ethane, and other gaseous, low molecular weight compounds.

It is believed that the reactions described herein are very selective. No formation of 2-propanethiol (isopropyl mercaptan) was observed during this experiment, which illustrates the selectivity of the reaction or the concerted reaction mechanism. It does not appear as if the normal propanol was dehydrated to an olefin, propylene, prior to being converted to the mercaptan. If this were the case, then with the subsequent addition of hydrogen sulfide to the propylene, 2-propanethiol (isopropyl mercaptan) would have been the major product.

Example 3

Conversion of Normal Butanol to 1-Butanethiol (n-Butyl Mercaptan)

1-Butanethiol (normal butyl mercaptan) (mercaptan stream) 18b was produced by reacting normal butanol (alcohol feed stream) 8b with hydrogen sulfide (sulfur compound reactant stream) 10b in the presence of the catalyst blend 5b described herein, as shown in FIG. 3. The resulting reaction is an exothermic reaction, as follows:

$$\text{n-}C_4H_9OH + H_2S \rightarrow \text{n-}C_4H_9SH + H_2O \quad \Delta H_{rxn} = -27,000 \text{ BTU/hr}$$

$$\text{n-}C_4H_9OH + \text{n-}C_4H_9SH \rightarrow H_9C_4SC_4H_9 + H_2O \quad \Delta H_{rxn} = -24,100 \text{ BTU/hr}$$

1-Butanethiol (n-butyl mercaptan) 18b was produced in a downflow fixed bed catalytic flow reactor. The catalyst used was the catalyst blend 5b of the hydrotreating catalyst A and an alumina diluent B. The hydrotreating catalyst A was a CoMo/alumina produced by Haldor Topsoe Inc. and is commercially available as TK-554. The hydrotreating catalyst A was diluted with an inert alpha (α)-alumina (alumina diluent) B produced by Norton Chemical Process and Products and is commercially available as 14 grit Alundum. The catalyst packing that was used had three equal zones (by volume). The first zone 12b contained about ½ by volume of the hydrotreating catalyst A and about ½ by volume alumina diluent B. The middle zone 14b contained about ¾ by volume of the hydrotreating catalyst A and about ½ by volume of the alumina diluent B. The last zone 16b contained 100% by volume of the hydrotreating catalyst A. The results of the example runs are shown in Table 3.

TABLE 3

Normal Butyl Mercaptan (NBM) Synthesis Results

| | | | Feed Properties and Conditions | | | | | | | Product Compositions | | | |
|---|---|---|---|---|---|---|---|---|---|---|---|---|---|
| Run Number | nButanol g/hr | H$_2$S g/hr | Press psig | L/D | cat g | catvol cc | WHSV | H$_2$S/nButanol molar feed ratio | WAT °C. | WAT °F. | nButanol area % | NBM area % | di-n-butyl ether area % | heavies area % |
| 1 | 19 | 99 | 450 | 22 | 62.9 | 112 | 0.30 | 11.6 | 235 | 455 | 62.8 | 14.3 | 4.1 | 18.8 |
| 2 | 19 | 99 | 450 | 22 | 62.9 | 112 | 0.30 | 11.6 | 245 | 473 | 60.5 | 17.7 | 7.6 | 14.2 |
| 3 | 19 | 99 | 450 | 22 | 62.9 | 112 | 0.30 | 11.6 | 255 | 491 | 45.5 | 25.5 | 7.8 | 21.2 |
| 4 | 19 | 99 | 450 | 22 | 62.9 | 112 | 0.30 | 11.6 | 258 | 496 | 24.5 | 34.5 | 7.9 | 33.1 |
| 5 | 19 | 99 | 450 | 22 | 62.9 | 112 | 0.30 | 11.6 | 268 | 514 | 14.5 | 36.8 | 8.4 | 40.3 |
| 6 | 19 | 99 | 450 | 22 | 62.9 | 112 | 0.30 | 11.6 | 268 | 514 | 7.1 | 39.0 | 0.3 | 53.6 |
| 7 | 19 | 99 | 450 | 22 | 63 | 112 | 0.30 | 11.3 | 180 | 356 | 72.3 | 6.6 | 0.0 | 21.2 |
| 8 | 19 | 99 | 450 | 22 | 63 | 112 | 0.30 | 11.3 | 180 | 356 | 82.7 | 7.0 | 0.0 | 10.3 |
| 9 | 19 | 99 | 450 | 22 | 63 | 112 | 0.30 | 11.3 | 200 | 392 | 71.7 | 17.2 | 0.0 | 11.1 |
| 10 | 19 | 99 | 450 | 22 | 63 | 112 | 0.30 | 11.3 | 200 | 392 | 52.6 | 36.1 | 0.0 | 11.3 |
| 11 | 19 | 99 | 450 | 22 | 63 | 112 | 0.30 | 11.3 | 220 | 428 | 49.1 | 35.2 | 0.0 | 15.7 |
| 12 | 19 | 99 | 450 | 22 | 63 | 112 | 0.30 | 11.3 | 220 | 428 | 31.8 | 51.3 | 0.0 | 16.9 |
| 13 | 19 | 99 | 450 | 22 | 63 | 112 | 0.30 | 11.3 | 220 | 428 | 31.6 | 50.7 | 0.0 | 17.8 |

The normal butanol (alcohol feed stream) 8b and the hydrogen sulfide (sulfur compound reactant stream) 10b were fed separately and controlled using mass flow controllers. Product compositions of the mercaptan stream 18b were monitored using an on-line gas chromatograph with a flame detector. The weight hourly space velocity (WHSV) was calculated based upon the normal butanol feed stream 8b feedrate.

Based upon the results shown in Table 3, the optimal process conditions include a weight average bed temperature (WAT) of about 240° C. As in the production of 1-propanethiol (normal propyl mercaptan), the catalyst blend was preheated to about 180° C. prior to introducing the feedstreams to the catalyst blend 5b. The optimal pressure range was about 450 psig to about 600 psig. The optimal normal butanol weight hourly space velocity (WHSV) was about 0.30 gr. liq./hr./gr. cat. and the hydrogen sulfide to normal butanol molar feed ratio was 12:1 or greater. In an aspect, the normal butanol WHSV ranges from about 0.25 to about 0.30 gr. liq./hr./gr. cat.

The highest conversion rate of normal butanol in this example was 92%. In order to achieve higher conversion rates, a lower weight hourly space velocity and slightly higher temperature would be required. No formation of 2-butanethiol (secondary butyl mercaptan) was observed, which supports the concept that the reaction is a concerted or selective reaction mechanism that selectively produced the normal isomer of butanethiol (butyl mercaptan).

Example 4

Conversion of Cyclohexanol to Cyclohexanethiol (Cyclohexyl Mercaptan)

In this example, cyclohexanethiol (cyclohexyl mercaptan) (mercaptan stream) 18 was produced from cyclohexanol (alcohol feed stream) 8 and hydrogen sulfide (sulfur compound reactant stream) 10 that were reacted in the presence of a catalyst blend 5, which contained a hydrotreating catalyst A and a dehydrating catalyst B, in a fixed bed flow reactor, as shown in FIG. 1. The hydrotreating catalyst A was a CoMo/alumina catalyst and the dehydrating catalyst B was a gamma (γ)-alumina catalyst. The catalyst blend 5 was divided into three zones. The three zones were the same used for the conversion of ethanol to ethenethiol (ethyl mercaptan) in Example 1 described herein.

The reactions that occurred during synthesis of cyclohexanethiol (cyclohexyl mercaptan) 18 from cyclohexanol 8 and hydrogen sulfide 10, were as follows:

For the reaction, cyclohexene$_{(l)}$+H$_2$S→CHM$_{(l)}$, ΔH= −35,300 BTU/lb mole.  1)

For the reaction, cyclohexanol$_{(g)}$→cyclohexene$_{(g)}$+ H$_2$O$_{(g)}$, ΔH=+17,121 BTU/lb mole.  2)

For the reaction, cyclohexanol$_{(l)}$+H$_2$S→CHM$_{(l)}$+H$_2$O $_{(l)}$, ΔH=−24,600 BTU/lb mole.  3)

For the reaction, cyclohexanol$_{(l)}$+H$_2$S→CHM$_{(l)}$+H$_2$O $_{(g)}$, ΔH=−5,700 BTU/lb mole.  4)

For the reaction, 3cyclohexene$_{(l)}$→benzene$_{(g)}$+2cyclohexane$_{(g)}$, ΔH=−21,400 BTU/lb mole.  5)

The results of this example are shown in Table 4.

TABLE 4

Cyclohexyl Mercaptan (CHM) Synthesis Results

| | Feed Conditions and Properties | | | | | | Product Compositions | | | | | |
|---|---|---|---|---|---|---|---|---|---|---|---|---|
| Run Number | Press psig | L/D | WHSV | H$_2$S/cyclohexanol molar feed ratio | WAT °C. | WAT °F. | cyclohexanol mole % | CHM Mole % | cyhexene mole % | cyhexane mole % | benzene mole % | Catalyst |
| 1 | 800 | 22 | 0.36 | 15.6 | 280 | 536 | 0.0 | 9.7 | 90.3 | 0.0 | 0.0 | γ-alumina |
| 2 | 800 | 22 | 0.36 | 15.6 | 180 | 356 | 91.4 | 2.0 | 6.7 | 0.0 | 0.0 | γ-alumina |
| 3 | 800 | 22 | 0.36 | 15.6 | 170 | 338 | 95.4 | 1.5 | 3.1 | 0.0 | 0.0 | γ-alumina |
| 4 | 500 | 22 | 0.38 | 15.1 | 200 | 392 | 91.7 | 3.3 | 5.0 | 0.0 | 0.0 | TK-554 |

TABLE 4-continued

Cyclohexyl Mercaptan (CHM) Synthesis Results

| | Feed Conditions and Properties | | | | | | Product Compositions | | | | | |
|---|---|---|---|---|---|---|---|---|---|---|---|---|
| Run Number | Press psig | L/D | WHSV | H$_2$S/cyclohexanol molar feed ratio | WAT ° C. | WAT ° F. | cyclohexanol mole % | CHM Mole % | cyhexene mole % | cyhexane mole % | benzene mole % | Catalyst |
| 5  | 600 | 22 | 0.38 | 15.1 | 225 | 437 | 93.9 | 2.5  | 3.6  | 0.0 | 0.0 | TK-554 |
| 6  | 700 | 22 | 0.25 | 15.1 | 260 | 500 | 3.30 | 76.3 | 18.8 | 1.6 | 0.0 | TK-554 |
| 7  | 700 | 22 | 0.25 | 15.1 | 280 | 536 | 0.0  | 80.4 | 16.8 | 1.7 | 0.9 | TK-554 |
| 8  | 700 | 22 | 0.25 | 15.1 | 300 | 572 | 0.0  | 77.3 | 17.7 | 3.5 | 1.5 | TK-554 |
| 9  | 700 | 22 | 0.18 | 15.1 | 260 | 500 | 0.0  | 91.6 | 2.7  | 4.7 | 1.0 | mixed |
| 10 | 700 | 22 | 0.18 | 15.1 | 270 | 518 | 0.0  | 86.0 | 3.5  | 8.9 | 1.7 | mixed |
| 11 | 700 | 22 | 0.15 | 15.1 | 225 | 437 | 0.0  | 96.3 | 2.2  | 1.5 | 0.0 | mixed |
| 12 | 700 | 22 | 0.15 | 15.1 | 240 | 464 | 0.0  | 95.8 | 2.5  | 1.8 | 0.0 | mixed |
| 13 | 700 | 22 | 0.25 | 8.9  | 240 | 464 | 0.0  | 94.7 | 3.6  | 1.7 | 0.0 | mixed |
| 14 | 700 | 22 | 0.37 | 8.9  | 240 | 464 | 0.0  | 94.5 | 3.9  | 1.7 | 0.0 | mixed |
| 15 | 700 | 22 | 0.46 | 5.6  | 240 | 464 | 0.0  | 92.7 | 5.1  | 2.2 | 0.0 | mixed |
| 16 | 700 | 22 | 0.52 | 5.6  | 240 | 464 | 0.0  | 92.6 | 5.0  | 2.4 | 0.0 | mixed |
| 17 | 500 | 22 | 0.43 | 5.9  | 240 | 464 | 0.0  | 89.2 | 8.6  | 2.1 | 0.0 | mixed |
| 18 | 500 | 22 | 0.50 | 5.9  | 240 | 464 | 0.0  | 89.5 | 8.4  | 2.1 | 0.0 | mixed |
| 19 | 500 | 22 | 0.61 | 4.0  | 240 | 464 | 0.0  | 88.2 | 9.5  | 2.4 | 0.0 | mixed |

The selectivity of cyclohexanol 8 to cyclohexanethiol (cyclohexyl mercaptan) 18 at 240° C. was as high as about 96%. The hydrogen sulfide 10 to cyclohexanol 8 molar feed ratio was varied from about 4:1 to about 16:1 during this example. No heavies were observed to be formed during any of the runs, even at the about 4:1 molar feed ratio. As the molar feed ratio was decreased, the selectivity for cyclohexanethiol (cyclohexyl mercaptan) 18 decreased gradually, as shown in Table 4. More cyclohexene and cyclohexane were produced at lower hydrogen sulfide 10 to cyclohexanol 8 molar feed ratios. Although more cyclohexene and cyclohexane were present, at 240° C., there was less than 0.1 mole % cyclohexanol 8 in the cyclohexanethiol (cyclohexyl mercaptan) 18 regardless of the hydrogen sulfide 10 to cyclohexanol 8 molar feed ratio.

The optimal process conditions in this example included a WAT of 240° C. and an hydrogen sulfide 10 to cyclohexanol 8 molar feed ratio of 9:1. The pressure should be at least 600 psig and the cyclohexanol space velocity (WHSV) should be 0.30 gr. liq./hr./gr. cat. for optimal conditions. The cyclohexanol space velocity (WHSV) ranged from about 0.15 gr. liq./hr./gr. cat. to about 0.61 gr. liq./hr./gr. cat. As long as the temperature was held constant at 240° C., no cyclohexanol 8 breakthrough occurred at any of the pressures or space velocities examined. At 230° C. and lower temperatures, cyclohexanol 8 breakthrough occurred.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

We claim:

1. A process for selective production of a mercaptan or a sulfide comprising the steps of:
   a) contacting an alcohol, a sulfur compound reactant having a formula of H—S—R, and a catalyst blend comprising a hydrotreating catalyst and a dehydration catalyst, R comprising H or an alkyl group; and
   b) reacting the alcohol and the sulfur compound reactant at a sulfur compound reactant to alcohol molar feed ratio that ranges from about 9:1 to about 20:1 to produce the mercaptan or the sulfide having less than about 30 wt. % unreacted alcohol contained therein; and wherein the hydrotreating catalyst comprises at least one Group IIIA-VIIIA transition metal and a support and the dehydration catalyst is gamma (γ)-alumina.

2. The process of claim 1, wherein:
   a) the alcohol is methanol, ethanol, 1-propanol, 2-propanol, cyclohexanol, 1-butanol, 2-butanol, or combinations thereof;
   b) the sulfur compound reactant is hydrogen sulfide, methanethiol, ethanethiol, or combinations thereof; and
   c) the mercaptan or the sulfide is ethanethiol, 2-propanethiol, cyclohexanethiol, 2-butanethiol, 2-thiopropane, 1-(methylthio)ethane, 1,1'-thiobisethane, or combinations thereof.

3. The process of claim 1, wherein the catalyst blend comprises about 40% by volume to about 95% by volume hydrotreating catalyst and about 5% by volume to about 60% by volume dehydration catalyst.

4. The process of claim 1, wherein the hydrotreating catalyst comprises:
   a) an oxide of molybdenum and art oxide of cobalt supported on alumina; or
   b) an oxide of molybdenum and an oxide of nickel supported on alumina.

5. A process for selective production of a mercaptan or a sulfide comprising the steps of:
   a) contacting an alcohol, a sulfur compound reactant having a formula of H—S—R, and a catalyst blend comprising a hydrotreating catalyst and an alumina diluent having a volumetric ratio of the hydrotreating catalyst to the alumina diluent that increases from an inlet of the diluted catalyst blend to an outlet of the diluted catalyst blend, R comprising H or an alkyl group, the hydrotreating catalyst being an oxide of molybdenum and an oxide of cobalt supported on alumina or an oxide of molybdenum and an oxide of nickel supported on alumina; and b) reacting the alcohol and the sulfur compound reactant to produce the mercaptan or the sulfide having less than about 30 wt. % unreacted alcohol contained therein;

wherein, the alumina diluent is alpha (Γ)-alumina.

6. The process of claim 5, wherein:
   a) the alcohol is methanol, 1-ethanol, 1-propanol, 2-propanol, cyclohexanol, phenol, 1-butanol, 2-butanol, 2-butyl-1-octanol, α-hydroxytoluene, 1,6-hexanediol, 1-phenyl-1-ethanol, 2-phenyl-1-ethanol, or combinations thereof;
   b) the sulfur compound reactant is hydrogen sulfide, methanethiol, ethanethiol, or combinations thereof; and
   c) the mercaptan or the sulfide is methanethiol, ethanethiol, 1-propanethiol, 2-propanethiol, cyclohexanethiol, 1-butanethiol, 2-butanethiol, 2-butyloctanethiol, benzenethiol, α-toluenethiol, 1,6-hexanedithiol, 1-phenyl-1-ethanethiol, 2-phenyl-1-ethanethiol, 2-thiopropane, 1-(methylthio)ethane, 1,1'-thiobisethane, or combinations thereof.

7. A process for selective production of a mercaptan or a sulfide comprising the steps of:
   a) contacting an alcohol, a sulfur compound reactant having a formula of H—S—R, and a catalyst blend comprising a hydrotreating catalyst and a dehydration catalyst or an alumina diluent, R comprising H or an alkyl group; and
   b) reacting the alcohol and the sulfur compound reactant to produce the mercaptan or the sulfide having less than about 30 wt. % unreacted alcohol contained therein, the catalyst blend having a volumetric ratio of the hydrotreating catalyst to the dehydration catalyst or the alumina diluent that increases from a reactor vessel inlet to a reactor vessel outlet in order to maintain near isothermal conditions during reaction of the alcohol and the sulfur compound reactant;

wherein, the hydrotreating catalyst comprising at least one Group IIIA-VIIIA transition metal and a support, the dehydration catalyst is gamma (γ)-alumina, and the alumina diluent is alpha (α)-alumina.

8. The process of claim 7, wherein the catalyst blend comprises about 40% by average volume to about 95% by average volume hydrotreating catalyst and about 5% by average volume to about 60% by average volume dehydration catalyst or alumina diluent.

9. The process of claim 7, wherein the hydrotreating catalyst comprises:
   a) an oxide of molybdenum and an oxide of cobalt supported on alumina; or
   b) an oxide of molybdenum and an oxide of nickel supported on alumina.

10. The process of claim 7, wherein:
    a) the alcohol is methanol, ethanol, 1-propanol, 2-propanol, cyclohexanol, 1-butanol, 2-butanol, or combinations thereof;
    b) the sulfur compound reactant is hydrogen sulfide, methanethiol, ethanethiol, or combinations thereof; and
    c) the mercaptan or the sulfide is ethanethiol, 2-propanethiol, cyclohexanethiol, 2-butanethiol, 2-thiopropane, 1-(methylthio)ethane, 1,1'-thiobisethane, or combinations thereof.

11. The process of claim 7, wherein:
    a) the alcohol is methanol, 1-ethanol, 1-propanol, 2-propanol, cyclohexanol, phenol, 1-butanol, 2-butanol, 2-butyl-1-octanol, α-hydroxytoluene, 1,6-hexanediol, 1-phenyl-1-ethanol, 2-phenyl-1-ethanol, or combinations thereof;
    b) the sulfur compound reactant is hydrogen sulfide, methanethiol, ethanethiol, or combinations thereof; and
    c) the mercaptan or the sulfide is methanethiol, ethanethiol, 1-propanethiol, 2-propanethiol, cyclohexanethiol, 1-butanethiol, 2-butanethiol, 2-butyloctanethiol, benzenethiol, α-toluenethiol, 1,6-hexanedithiol, 1-phenyl-1-ethanethiol, 2-phenyl-1-ethanethiol, 2-thiopropane, 1-(methylthio)ethane, 1,1'-thiobisethane, or combinations thereof.

12. The process of claim 7, wherein the reactor vessel comprises at least three zones, wherein:
    a) the volumetric ratio of a first zone is in a range of about 1:0.75 to about 1:3.25;
    b) the volumetric ratio of a second zone is in a range of about 4:1 to about 1.25:1; and
    c) the volumetric ratio of a last zone is in a range of about 1:0 to about 3:2.

13. The process of claim 12, wherein:
    a) the volumetric ratio of the first zone is about 1:2;
    b) the volumetric ratio of the second zone is about 1:1;
    c) the volumetric ratio of the last zone is about 1:0;
    d) the alcohol is cyclohexanol, methanol, or combinations thereof; and
    e) the mercaptan is cyclohexanethiol, ethanethiol, or combinations thereof.

14. The process of claim 12, wherein:
    a) the volumetric ratio of the first zone is about 1:1;
    b) the volumetric ratio of the second zone is about 3:1;
    c) the volumetric ratio of the last zone is about 1:0;
    d) the alcohol is 1-butanol, methanol, ethanol, or combinations thereof; and
    e) the mercaptan or the sulfide is 1-butanethiol, 1-(methylthio)ethane, 1,1'-thiobisethane, or combinations thereof.

15. The process of claim 12, wherein:
    a) the volumetric ratio of the first zone is about 1:3;
    b) the volumetric ratio of the second zone is about 1:1;
    c) the volumetric ratio of the last zone is about 3:2;
    d) the alcohol is 1-propanol; and
    e) the mercaptan is 1-propanethiol.

* * * * *